United States Patent
Bartra Sanmartí et al.

(10) Patent No.: US 9,073,899 B2
(45) Date of Patent: Jul. 7, 2015

(54) SOLID FORMS OF DABIGATRAN ETEXILATE MESYLATE AND PROCESSES FOR THEIR PREPARATION

(71) Applicant: ESTEVE QUÍMICA, S.A., Barcelona (ES)

(72) Inventors: Martí Bartra Sanmartí, Barcelona (ES); Rosa Maria Espinosa Ferrer, Barberà Del Vallès (ES); Maria del Pilar Lupon Roses, Barcelona (ES); Stephen Benedict David Winter, Santa Coloma De Cervelló (ES); Silvia Donnici Garcia, Barcelona (ES)

(73) Assignee: ESTEVE QUÍMICA, S.A., Barcelona (ES)

( * ) Notice: Subject to any disclaimer, the term of this patent is extended or adjusted under 35 U.S.C. 154(b) by 0 days.

(21) Appl. No.: 14/376,834

(22) PCT Filed: Feb. 21, 2013

(86) PCT No.: PCT/EP2013/053499
§ 371 (c)(1),
(2) Date: Aug. 5, 2014

(87) PCT Pub. No.: WO2013/124385
PCT Pub. Date: Aug. 29, 2013

(65) Prior Publication Data
US 2015/0038721 A1 Feb. 5, 2015

Related U.S. Application Data

(60) Provisional application No. 61/607,741, filed on Mar. 7, 2012.

(30) Foreign Application Priority Data

Feb. 23, 2012 (EP) .................................... 12382065

(51) Int. Cl.
C07D 401/12 (2006.01)
A61K 31/4439 (2006.01)

(52) U.S. Cl.
CPC ........... C07D 401/12 (2013.01); *C07B 2200/13* (2013.01)

(58) Field of Classification Search
CPC ......................... C07D 401/12; A61K 31/4439
USPC ........................................ 546/273.4; 514/338
See application file for complete search history.

(56) References Cited

U.S. PATENT DOCUMENTS

2007/0185333 A1  8/2007  Zerban et al.

FOREIGN PATENT DOCUMENTS

| DE | 102005061623 | | 6/2007 |
|---|---|---|---|
| WO | WO 98/37075 | | 8/1998 |
| WO | WO 03/074056 | | 9/2003 |
| WO | WO 2005/028468 | | 3/2005 |
| WO | WO 2011/110478 | | 9/2011 |
| WO | WO 2011/110876 | | 9/2011 |
| WO | 2012/027543 | * | 3/2012 |

OTHER PUBLICATIONS

Assessment Report for Pradaxa of the Committee for Human Medicinal Products (CHMP) of the European Medicines Agency (EMEA/174363/2008), 2008.
International Search Report and Written Opinion of the International Search Authority for PCT/EP2013/053499, Oct. 16, 2013.

* cited by examiner

*Primary Examiner* — Patricia L Morris
(74) *Attorney, Agent, or Firm* — Squire Patton Boggs (US) LLP (57) ABSTRACT

It relates to solid forms of dabigatran etexilate mesylate, in particular dabigatran etexilate mesylate in crystalline Form A, and in amorphous form; to processes for their preparation, and to pharmaceutical compositions comprising them. It also relates to a crystalline form of dabigatran etexilate base (Form A), and to a process for its preparation.

6 Claims, 4 Drawing Sheets

SOLID FORMS OF DABIGATRAN ETEXILATE MESYLATE AND PROCESSES FOR THEIR PREPARATION

RELATED APPLICATIONS

This application is a national stage entry of International Patent Application No. PCT/EP2013/053499 filed on Feb. 21, 2013, which claims the benefit of European Patent Application EP 12382065.6 filed on Feb. 23, 2012 and U.S. Provisional Patent Application Ser. No. 61/607,741 filed on Mar. 7, 2012, which are incorporated by reference herein in their entirety.

The present invention relates to new solid forms of dabigatran etexilate mesylate, to a process for their preparation, and to pharmaceutical compositions comprising them.

BACKGROUND ART

Dabigatran is the generic name of compound N-[([(amidinophenyl)-amino]methyl)-1-methyl-1H-benzimidazole-5-carbonyl]-N-(2-pyridyl)-3-aminopropionic acid, the chemical structure of which is the following:

Dabigatran is a thrombin specific inhibitor that is given orally in the form of the prodrug dabigatran etexilate. The latter is rapidly absorbed after oral administration and converts to dabigatran, the pharmacologically active molecule, through hydrolysis catalyzed by plasma and liver esterases. The chemical name for dabigatran etexilate is ethyl N—[([([(N'-hexyloxycarbonyl)-amidino]phenyl)amino]methyl)-1-methyl-1H-benzimidazole-5-carbonyl]-N-(2-pyridyl)-3-aminopropionate, and its chemical structure is the following:

Dabigatran and dabigatran etexilate base were first described in patent application WO 98/37075. The mesylate salt of dabigatran etexilate was described in WO 03/74056. In particular example 3 of this document discloses the preparation of dabigatran etexilate mesylate. The resulting product is obtained in a crystalline form characterized by a melting point of 178-179° C. Reproduction of this example by the inventors of the present invention results in a product which corresponds to the crystalline Form I disclosed in WO 2005/028468.

Document WO 2005/028468 discloses two different anhydrous crystalline forms and a hydrated form of dabigatran etexilate mesylate. The crystalline anhydrous forms include Form I, having a melting point of 180±3° C.; and Form II, having a melting point of 190±3° C. The hydrated form has a melting point of 120±5° C.

Document WO 2011/110876 describes in example 15 the preparation of dabigatran etexilate mesylate Form IV characterized by a specific powder X-ray diffraction pattern and by having a melting point of 167-169° C. Reproduction of this example by the inventors of the present invention results in a product which corresponds to the crystalline Form I disclosed in WO 2005/028468.

Document WO 2011/110478 discloses two different non-crystalline forms of dabigatran etexilate mesylate: a solid solution comprising a solid solvent and dabigatran etexilate mesylate dissolved therein; and an amorphous form of dabigatran etexilate mesylate as a composition with one or more hydrophilic polymers, wherein the hydrophilic polymer stabilizes the amorphous state of the active ingredient particles.

The different solid forms of a pharmaceutically active ingredient can have different characteristics, and offer certain advantages, for example with regard to stability, solubility or bioavailability. Thus, the discovery of new solid forms allows for improving the characteristics of the pharmaceutical formulations of the active ingredients, since some forms are more adequate for one type of formulation, and other forms for other different formulations. Furthermore, depending on the therapeutic indications, one or another pharmaceutical formulation may be preferred. It is hence of interest to have new solid forms of dabigatran etexilate mesylate.

SUMMARY OF THE INVENTION

The inventors have surprisingly found new crystalline forms of dabigatran etexilate mesylate which show high stability. This ensures that the solid form of the drug does not change in the pharmaceutical preparation later produced from it, which guarantees the reproducible potency of the drug.

An advantage of the solid forms of the invention is that they have physico-mechanical properties that allow for good manipulation for the preparation of solid pharmaceutical formulations.

Another advantage of the solid forms of the present invention lies in the fact that they are obtained with high yields and high purity.

Therefore, an aspect of the present invention relates to a crystalline Form A of dabigatran etexilate mesylate, which is characterized by having an X-ray diffractogram that comprises characteristic peaks at 4.4, 8.9, 9.8, 12.3, 17.8, 18.4, 19.2, 19.7, 21.4, 23.4, 27.3, 28.2±0.1 degrees 2 theta measured in an X-ray diffractometer with Cu Kα radiation (1.5418 Å).

Further aspects of the present invention refer to several processes for the preparation of the crystalline Form A of dabigatran etexilate mesylate.

The present invention also relates to a pharmaceutical composition comprising the crystalline Form A of dabigatran etexilate mesylate, as well as to its use in the treatment and/or prophylaxis of thrombotic diseases.

Another aspect of the present invention relates to an amorphous form of dabigatran etexilate mesylate. Further aspects of the present invention refer to several processes for the preparation of the amorphous form of dabigatran etexilate mesylate.

The present invention also relates to a pharmaceutical composition comprising the amorphous form of dabigatran etexilate mesylate, as well as to its use in the treatment and/or prophylaxis of thrombotic diseases.

Further aspects of the present invention relate to a crystalline Form A of dabigatran etexilate base characterized by having an X-ray diffractogram that comprises characteristic peaks at 7.6, 10.5, 11.7, 13.2, 13.5, 15.3, 16.8, 17.6, 18.3, 21.0, 22.6, 22.9, 23.8, 25.5, 25.8, 26.5, 27.7±0.1 degrees 2 theta measured in an X-ray diffractometer with Cu Kα radiation (1.5418 Å); and to a process for its preparation.

DETAILED DESCRIPTION OF THE INVENTION

As mentioned above, the crystalline Form A of dabigatran etexilate mesylate shows improved stability with regard to the known crystalline forms I and II of dabigatran etexilate mesylate. In this regard, it is to be noted that the marketed dabigatran etexilate mesylate (Pradaxa) is mainly in the crystalline Form I and could be partly in the crystalline Form II according to the Assessment Report for Pradaxa of the Committee for Human Medicinal Products (CHMP) of the European Medicines Agency (EMEA/174363/2008). From the perspective of stability of the formulated product, it is clearly advantageous to choose a crystalline form of the active pharmaceutical ingredient that has favorable stability characteristics.

The improved stability characteristics of the crystalline Form A of dabigatran etexilate mesylate is demonstrated in the examples. In particular, a mixture of forms A and I of dabigatran etexilate mesylate (Example 6), and a mixture of forms A and II of dabigatran etexilate mesylate (Example 7) are converted entirely into Form A of dabigatran etexilate mesylate by means of solvent mediated transformation at room temperature. Additionally, whereas dabigatran etexilate mesylate Form A is stable after slurrying it in acetonitrile at room temperature (Example 12), crystalline form I of dabigatran etexilate mesylate is converted entirely into Form A under the same conditions (Example 8).

As mentioned above, the present invention relates to a crystalline Form A of dabigatran etexilate mesylate, which is characterized by having an X-ray diffractogram that comprises characteristic peaks at 4.4, 8.9, 9.8, 12.3, 17.8, 18.4, 19.2, 19.7, 21.4, 23.4, 27.3, 28.2±0.1 degrees 2 theta measured in an X-ray diffractometer with Cu Kα radiation (1.5418 Å).

Figure 2:
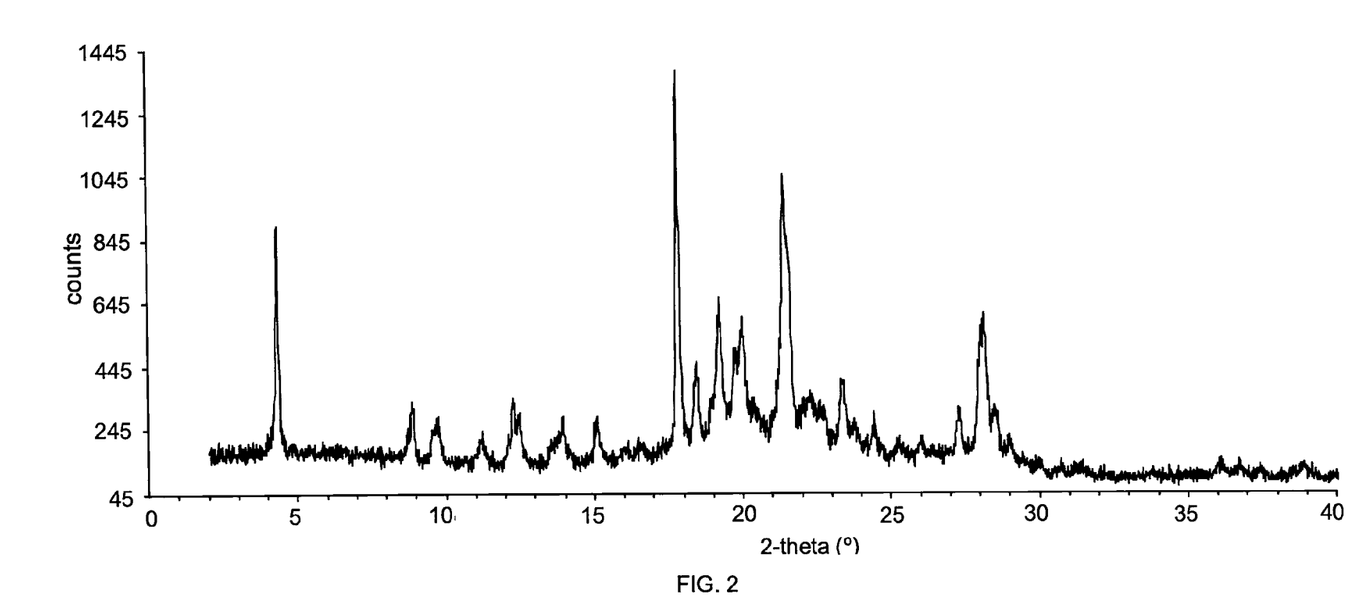
FIG. 2 shows the powder X-ray diffraction pattern (intensity (counts) vs. 2-theta angle (°)) of the crystalline Form A of dabigatran etexilate mesylate.

In one embodiment of the invention, the crystalline Form A of dabigatran etexilate mesylate is characterized by having an X-ray diffractogram as shown in FIG. 2. This diffractogram differs from the ones of other solid forms of dabigatran etexilate mesylate known in the state of the art. In another particular embodiment, the crystalline Form A of dabigatran etexilate mesylate is characterized by having an X-ray diffractogram that comprises the characteristic peaks at the values shown in Table 1±0.1 degrees 2 theta measured in an X-ray diffractometer with Cu Kα radiation (1.5418 Å).

TABLE 1

| 2θ (°) | d (Å) | Intensity (%) |
|---|---|---|
| 4.4 | 20.2 | 64 |
| 8.9 | 10.0 | 22 |
| 9.8 | 9.1 | 18 |
| 11.2 | 7.9 | 15 |
| 12.3 | 7.2 | 22 |
| 12.5 | 7.1 | 19 |
| 14.0 | 6.3 | 18 |
| 15.1 | 5.9 | 18 |
| 17.8 | 5.0 | 100 |
| 18.4 | 4.8 | 31 |
| 19.2 | 4.6 | 46 |
| 19.7 | 4.5 | 34 |
| 20.0 | 4.4 | 42 |
| 21.4 | 4.1 | 76 |
| 23.4 | 3.8 | 27 |
| 27.3 | 3.3 | 20 |
| 28.2 | 3.2 | 42 |
| 28.5 | 3.1 | 21 |

The crystalline Form A of dabigatran etexilate mesylate may be obtained by several processes which also form part of the invention.

Thus, a first process for preparing the crystalline Form A of dabigatran etexilate mesylate comprises:

a) providing a solution of dabigatran etexilate mesylate in an organic solvent;

b) optionally seeding with dabigatran etexilate mesylate, Form A; and c) isolating the crystalline Form A of dabigatran etexilate mesylate from the reaction medium.

In a preferred embodiment of this first process, the organic solvent is selected from the group consisting of ($C_1$-$C_5$)alcohols, ($C_1$-$C_6$)alkyl($C_1$-$C_6$)alkanoates, ($C_3$-$C_8$)ketones, ($C_3$-$C_6$)ethers and ($C_2$-$C_4$)nitriles. In a more preferred embodiment, step a) is performed in an organic solvent selected from the group consisting of ethanol, n-butanol and acetonitrile at a temperature comprised between 0° C. and the reflux temperature of the solvent. In a more preferred embodiment, step a) is performed in an organic solvent selected from ethanol, n-butanol and acetonitrile at a temperature comprised between 20 and 70° C.

It is clear to one skilled in the art that the starting solution of dabigatran etexilate mesylate may be obtained by a number of methods, including, but not limited to, preparation in-situ from dabigatran etexilate and methane sulfonic acid, or by dissolution of pre-formed dabigatran etexilate mesylate. In either case, the starting solid forms of dabigatran etexilate or dabigatran etexilate mesylate respectively, are irrelevant since the process passes through a solution phase. Therefore, any crystalline or amorphous form of dabigatran etexilate mesylate as the starting material would result in the same solid form of the product.

In another preferred embodiment of the first process, the crystalline Form A of dabigatran etexilate mesylate is obtained by the process comprising:

a) providing a solution of dabigatran etexilate mesylate in ethanol at a temperature comprised between 50-70° C.;

b) optionally seeding with dabigatran etexilate mesylate Form A; and c) isolating the crystalline Form A of dabigatran etexilate mesylate from the reaction medium.

In a particular embodiment, step a) of the above process comprises dissolving dabigatran etexilate mesylate in ethanol at a temperature of 50° C. In another particular embodiment, the process comprises seeding with dabigatran etexilate mesylate Form A.

In another preferred embodiment of the first process, the solution of step a) is obtained by reacting methanesulfonic acid and dabigatran etexilate base in an organic solvent. In a more preferred embodiment, the organic solvent is selected from the group consisting of ethanol, n-butanol and acetonitrile at a temperature comprised between 0° C. and the reflux temperature of the solvent.

In another preferred embodiment of the first process, the crystalline Form A of dabigatran etexilate mesylate is obtained by the process comprising:

a) reacting methanesulfonic acid and dabigatran etexilate base in ethanol at room temperature (20-25° C.); and b) isolating the crystalline Form A of dabigatran etexilate mesylate from the reaction medium.

In another preferred embodiment of the first process, the crystalline Form A of dabigatran etexilate mesylate is obtained by the process comprising:

a) reacting methanesulfonic acid and dabigatran etexilate base in acetonitrile or n-butanol at 50-70° C.; and b) isolating the crystalline Form A of dabigatran etexilate mesylate from the reaction medium.

A second process for preparing the crystalline Form A of dabigatran etexilate mesylate comprises:

a) providing a suspension of dabigatran etexilate mesylate, which is a pure solid form or a mixture of solid forms, in an organic solvent;

b) optionally seeding with dabigatran etexilate mesylate, Form A; and c) isolating the crystalline form A of dabigatran etexilate from the reaction medium.

In a preferred embodiment of the second process, the organic solvent is selected from the group consisting of ($C_1$-$C_5$)alcohols, ($C_1$-$C_6$)alkyl($C_1$-$C_6$)alkanoates, ($C_3$-$C_8$)ketones, ($C_3$-$C_6$)ethers and ($C_2$-$C_4$)nitriles. In a more preferred embodiment step a) is performed in an organic solvent selected from isopropyl alcohol, acetonitrile, acetone and 2-butanone at a temperature comprised between 0° C. and the reflux temperature of the solvent.

Since form A has the favourable property of being the most stable of the known forms of dabigatran etexilate mesylate, any of these other solid forms, or mixtures thereof, may be converted to form A by this second process.

In another preferred embodiment of the second process, the preparation of the crystalline Form A of dabigatran etexilate mesylate comprises:

a) providing a suspension of a mixture of crystalline Form I and crystalline Form A of dabigatran etexilate mesylate in 2-propanol at room temperature (20-25° C.); and b) isolating the crystalline Form A of dabigatran etexilate mesylate from the reaction medium.

In another preferred embodiment of the second process, the preparation of the crystalline Form A of dabigatran etexilate mesylate comprises:

a) providing a suspension of a mixture of crystalline Form II and crystalline Form A of dabigatran etexilate mesylate in 2-propanol at room temperature (20-25° C.); and b) isolating the crystalline Form A of dabigatran etexilate mesylate from the reaction medium.

In another preferred embodiment of the second process, the preparation of the crystalline Form A of dabigatran etexilate mesylate comprises:

a) providing a suspension of dabigatran etexilate mesylate in crystalline Form I in acetonitrile at room temperature (20-25° C.); and b) isolating the crystalline Form A of dabigatran etexilate mesylate from the reaction medium.

In another preferred embodiment of the second process, the preparation of the crystalline Form A of dabigatran etexilate mesylate comprises:

a) providing a suspension of dabigatran etexilate mesylate in crystalline Form I in acetone or 2-butanone;

b) seeding with dabigatran etexilate mesylate Form A; and c) isolating the crystalline Form A of dabigatran etexilate mesylate from the reaction medium.

The crystalline forms I and II of dabigatran etexilate mesylate mentioned above are disclosed in WO 2005/028468 and may be prepared by the process described in this document. The crystalline Form I and the crystalline Form II of dabigatran etexilate mesylate are characterized by having an X-ray diffractogram as disclosed in WO 2005/028468. Form I can also be obtained by the process described in WO 03/74056.

In another preferred embodiment of the second process, the preparation of the crystalline Form A of dabigatran etexilate mesylate comprises:

a) providing a suspension of dabigatran etexilate mesylate in amorphous form in acetonitrile at room temperature (20-25° C.); and b) isolating the crystalline Form A of dabigatran etexilate mesylate from the reaction medium.

The amorphous form of step a) may be obtained by the processes mentioned below or by any other suitable process, such as for example, spray drying.

In all the above processes which comprise slurrying a solid form or a mixture of solid forms, the slurrying step is carried out for the period of time necessary to complete the conversion of the starting solid form into crystalline Form A of dabigatran etexilate mesylate. This period of time may depend on several parameters, such as the temperature, the volume of the solvent, or the amount of Form A initially present in the mixture of crystalline forms. The skilled person would know how to adjust the parameters of each process in the light of the description and examples of the present invention.

Some of the processes above for the preparation of the crystalline Form A of dabigatran etexilate mesylate optionally include a step of seeding with dabigatran etexilate mesylate Form A. The seed crystal may be obtained by the process above without seeding; or by any of the processes below.

In all the above processes for the preparation of the crystalline Form A of dabigatran etexilate mesylate, the isolation of the product from the reaction medium can be carried out by several methods know in the art, such as filtration or centrifugation. In a particular embodiment, the separation is carried out by filtration. In another particular embodiment, the isolation comprises a previous step of cooling the reaction medium to a temperature comprised between 0° C. and room temperature, preferably between 0-5° C., whereby the product crystallizes.

Further, the isolated crystalline Form A of dabigatran etexilate mesylate may be dried. Drying may be achieved optionally under vacuum at a suitable temperature, preferably comprised between room temperature and 60° C.

The present invention also relates to a pharmaceutical composition comprising the crystalline Form A of dabigatran etexilate mesylate as defined herein, together with one or more pharmaceutically acceptable excipients or carriers.

It also forms part of the invention the crystalline Form A of dabigatran etexilate mesylate as defined herein for use in the treatment and/or prophylaxis of thrombotic diseases. It forms also part of the invention the use of the crystalline Form A of dabigatran etexilate mesylate for the manufacture of a medicament for the treatment and/or prophylaxis of thrombotic diseases. The present invention also relates to a method for the treatment and/or prophylaxis of thrombotic diseases, comprising administering a pharmaceutically effective amount of the crystalline Form A of dabigatran etexilate mesylate, together with pharmaceutically acceptable excipients or carriers, in a subject in need thereof, including a human.

The expression "therapeutically effective amount" as used herein, refers to the amount of a compound that, when administered, is sufficient to prevent development of, or alleviate to some extent, one or more of the symptoms of the disease which is addressed. The particular dose of compound administered according to this invention will of course be determined by the particular circumstances surrounding the case, including the compound administered, the route of administration, the particular condition being treated, and the similar considerations.

The expression "pharmaceutically acceptable excipients or carriers" refers to pharmaceutically acceptable materials, compositions or vehicles. Each component must be pharmaceutically acceptable in the sense of being compatible with the other ingredients of the pharmaceutical composition. It must also be suitable for use in contact with the tissue or organ of humans and animals without excessive toxicity, irritation, allergic response, immunogenicity or other problems or complications commensurate with a reasonable benefit/risk ratio.

Figure 3:
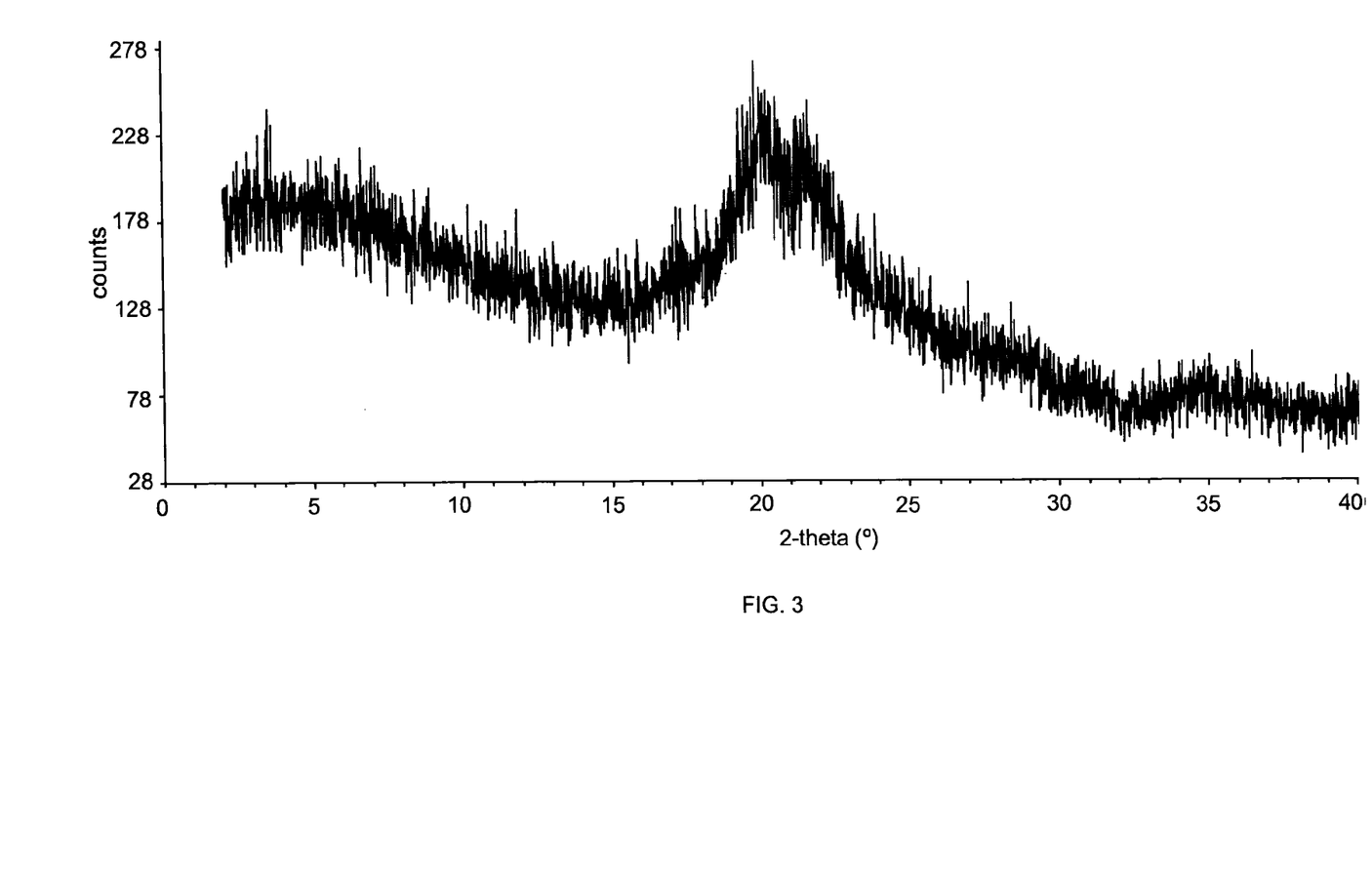
FIG. 3 shows the powder X-ray diffraction pattern (intensity (counts) vs. 2-theta angle (°)) of the amorphous form of dabigatran etexilate mesylate.

The invention further relates to an amorphous form of dabigatran etexilate mesylate. In particular, the invention relates to an amorphous form of dabigatran etexilate mesylate which is different from a composition comprising dabigatran etexilate mesylate in an amorphous form and one or more hydrophilic polymers. In a particular embodiment, the amorphous form of dabigatran etexilate mesylate is characterized by an X-ray diffractogram as in FIG. 3.

According to the prior art, the amorphous form of dabigatran needs to be stabilized by a hydrophilic polymer. However, the inventors have surprisingly found that it is possible to obtain an amorphous form, which is both physically and chemically stable, without the need of adding stabilizing agents. This has the advantage that the product, as well as the process for its preparation, are simplified.

Further, the amorphous form of dabigatran etexilate mesylate of the present invention is advantageous with respect to crystalline forms due to its enhanced solubility characteristics. Since dabigatran etexilate mesylate belongs to the Biopharmaceutics Classification System (BCS) class II, an improvement of the solubility should increase its bioavailability. As a consequence, with the amorphous form of the invention, higher bioavailability in comparison to the crystalline forms should be achieved.

The favourable solubility characteristics of the amorphous form of the invention, in particular with regard to other crystalline forms of dabigatran etexilate mesylate, is demonstrated in the examples. Thus, 50 mg of the amorphous form are completely dissolved in 1 mL acetonitrile at room temperature (20-25° C.) (example 9), whereas Forms I and A are at least partly insoluble under the same conditions (examples 8 and 12 respectively).

The present invention also provides processes for the preparation of the amorphous form of dabigatran etexilate mesylate. Thus, a first process comprises:

a) providing a solution of dabigatran etexilate mesylate in water or tert-butanol; and b) freeze-drying the solution.

A second process for the preparation of the amorphous form comprises:

a) providing a solution of dabigatran etexilate mesylate in methanol; and b) evaporating the solution to dryness.

In a preferred embodiment, step b) is carried out under vacuum.

Further, the isolated amorphous form of dabigatran etexilate mesylate may be dried. Drying may be achieved optionally under vacuum at a suitable temperature, preferably at room temperature (20-25° C.).

Figure 4:
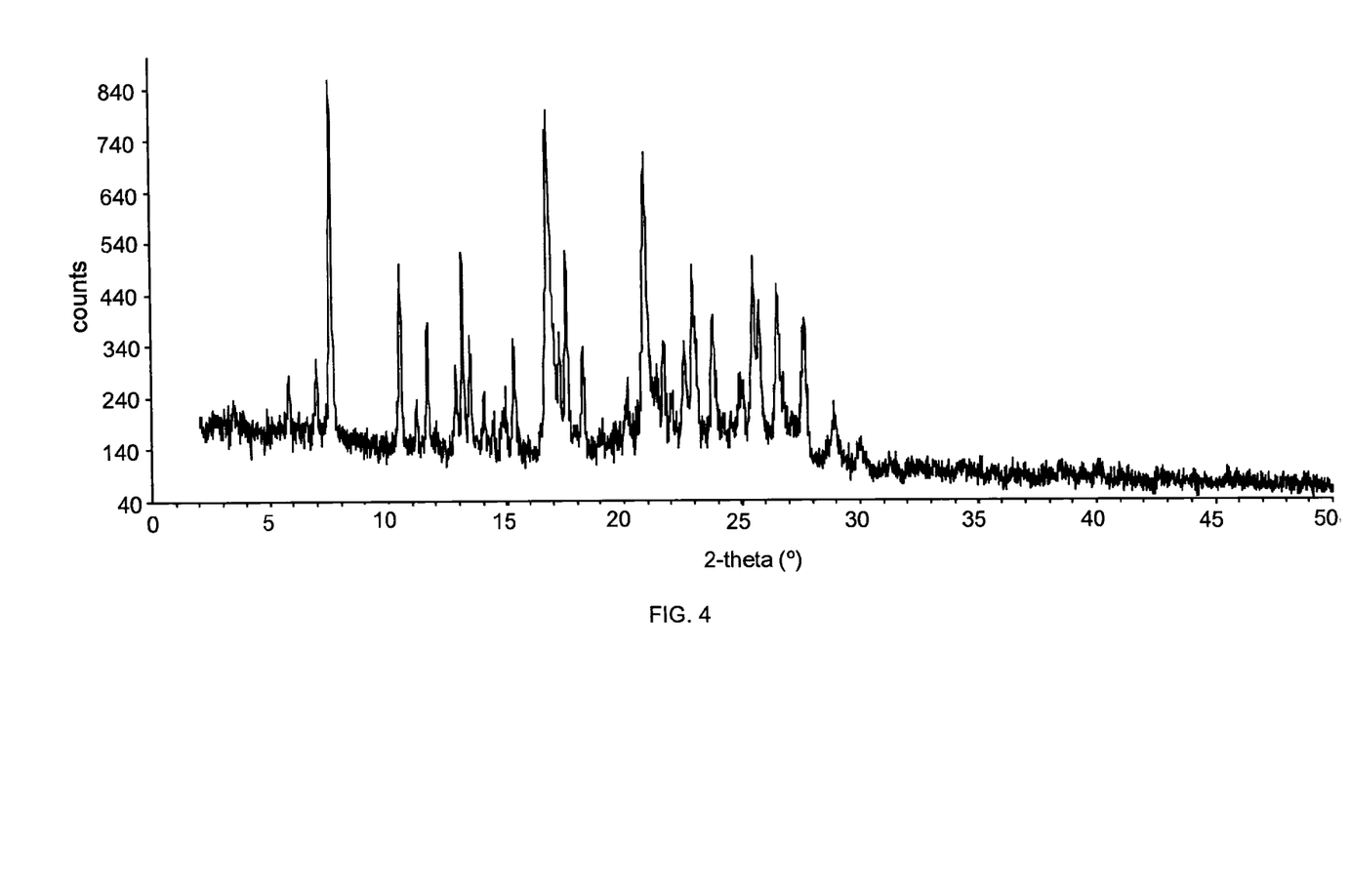
FIG. 4 shows the powder X-ray diffraction pattern (intensity (counts) vs. 2-theta angle (°)) of the crystalline Form A of dabigatran etexilate base.

Moreover, as mentioned above, the present invention also provides a new crystalline form of dabigatran etexilate base (Form A), characterized by having an X-ray diffractogram that comprises characteristic peaks at 7.6, 10.5, 11.7, 13.2, 13.5, 15.3, 16.8, 17.6, 18.3, 21.0, 22.6, 22.9, 23.8, 25.5, 25.8, 26.5, 27.7±0.1 degrees 2 theta measured in an X-ray diffractometer with Cu Kα radiation (1.5418 Å). In a particular embodiment, the Form A of dabigatran etexilate base is characterized by having an X-ray diffractogram as shown in FIG. 4. In another particular embodiment, the crystalline Form A of dabigatran etexilate base is characterized by having an X-ray diffractogram that comprises the characteristic peaks at the values shown in Table 2±0.1 degrees 2 theta measured in an X-ray diffractometer with Cu Kα radiation (1.5418 Å).

TABLE 2

| 2θ (°) | d (Å) | Intensity (%) |
|---|---|---|
| 3.5 | 25.5 | 24 |
| 5.8 | 15.1 | 30 |
| 7.0 | 12.6 | 34 |
| 7.6 | 11.6 | 100 |
| 10.5 | 8.4 | 56 |
| 11.2 | 7.9 | 24 |
| 11.7 | 7.6 | 42 |
| 12.9 | 6.9 | 32 |
| 13.2 | 6.7 | 59 |
| 13.5 | 6.6 | 39 |
| 14.1 | 6.3 | 26 |
| 14.5 | 6.1 | 21 |
| 15.0 | 5.9 | 27 |
| 15.3 | 5.8 | 38 |
| 16.8 | 5.3 | 92 |
| 17.3 | 5.1 | 40 |
| 17.6 | 5.0 | 59 |
| 18.3 | 4.9 | 36 |
| 20.2 | 4.4 | 29 |
| 21.0 | 4.2 | 82 |

TABLE 2-continued

| 2θ (°) | d (Å) | Intensity (%) |
|---|---|---|
| 21.7 | 4.1 | 37 |
| 22.0 | 4.0 | 25 |
| 22.6 | 3.9 | 37 |
| 22.9 | 3.9 | 56 |
| 23.8 | 3.7 | 44 |
| 24.9 | 3.6 | 30 |
| 25.5 | 3.5 | 58 |
| 25.8 | 3.5 | 47 |
| 26.5 | 3.4 | 51 |
| 27.7 | 3.2 | 43 |
| 28.9 | 3.1 | 23 |

Differential Scanning calorimetry (DSC) thermogram for the crystalline Form A of dabigatran etexilate base shows endothermic peak with onset at about 130° C.

The crystalline Form A of dabigatran etexilate base may be prepared by the process comprising:

a) providing a solution of dabigatran etexilate base in methyl tert-butyl ether at a temperature comprised between 40° C. and the reflux temperature of the solvent; and b) isolating the crystalline Form A of dabigatran etexilate base.

The isolation of crystalline Form A of dabigatran etexilate base may be carried out analogously as described for the crystalline Form A of dabigatran etexilate mesylate. Further, the isolated crystalline Form A of dabigatran etexilate base may be dried optionally under vacuum at a suitable temperature, preferably under vacuum at room temperature.

In the above process, the starting solid form of dabigatran etexilate base is irrelevant since the starting solid form is completely dissolved. Therefore, any crystalline or amorphous form of dabigatran etexilate base as the starting material would result in the same solid form of the product. For example, the starting material may be dabigatran etexilate base either as a 2-propanol solvate or as an amorphous solid.

Throughout the description and claims the word "comprise" and variations of the word, are not intended to exclude other technical features, additives, components, or steps. Furthermore, the word "comprise" encompasses the case of "consisting of". Additional objects, advantages and features of the invention will become apparent to those skilled in the art upon examination of the description or may be learned by practice of the invention. The following examples and drawings are provided by way of illustration, and they are not intended to be limiting of the present invention. Furthermore, the present invention covers all possible combinations of particular and preferred embodiments described herein.

EXAMPLES

Powder X-Ray Diffraction (XRD)

Powder diffraction patterns were acquired using a PANalytical, X'Pert diffractometer using CuKalpha-radiation. The system was configured in theta-theta, transmission geometry equipped with a focusing X-ray mirror and PIXcel detector.

Differential Scanning Calorimetry (DSC)

DSC analyses were recorded using a Mettler Toledo DSC822e. Samples of 5 to 7 mg were prepared in a perforated aluminium capsule, and were heated under nitrogen flow (60 mL/min), at a heating rate of 5° C./min. Data collection and evaluation were performed with STARe software.

High-Pressure Liquid Chromatography (HPLC)

HPLC analyses were performed uning the following conditions:

Column: Symmetry C18 (150×4.6 mm; 5 μm)
Flow: 1 mL/min
Injection volume: 10 μL
Temperature: 25° C.
UV detection: 300 nm
Sample dissolved in acetonitrile (1 mg/mL)
Eluent A: Aqueous solution of ammonium acetate 10 mM (adjusted to pH 7.5 with diluted $NH_4OH$)
Eluent B: Acetonitrile (HPLC grade)
Gradient:

| Time (min) | % B | % A |
|---|---|---|
| 0 | 30 | 70 |
| 13 | 70 | 30 |
| 18 | 70 | 70 |
| 20 | 30 | 30 |

Preparation of Dabigatran Etexilate Mesylate According to WO 03/74056

Figure 1:
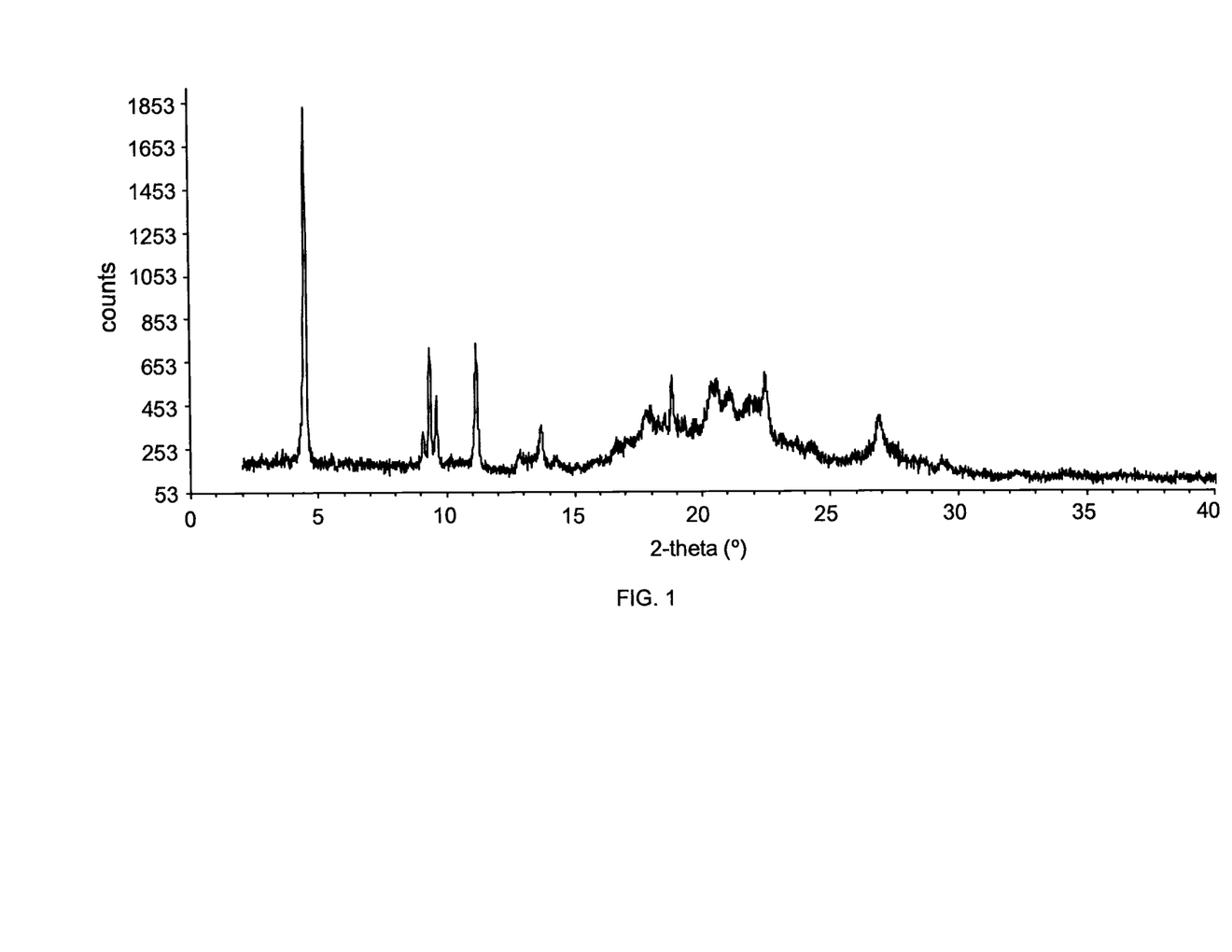
FIG. 1 shows the powder X-ray diffraction pattern (intensity (counts) vs. 2-theta angle (°)) of the crystalline Form I of dabigatran etexilate mesylate known in the art.

Methanesulfonic acid (15 mg) in ethyl acetate (EtOAc) (0.8 mL) was added dropwise to dabigatran etexilate base (100 mg) in EtOAc (8 mL) at ambient temperature with stirring. Precipitation was observed within 10 minutes of the addition. The mixture was stirred for one hour and then cooled to 0° C. and stirred for another hour before filtering, washing with EtOAc (1.6 mL) and ether (1.6 mL). The solid was dried in a circulating hot air oven at 50° C. for 16 hours. The product was analysed by XRD (FIG. 1) and confirmed to be dabigatran etexilate mesylate Form I (HPLC purity: 97.2%).

Example 1

Preparation of Amorphous Dabigatran Etexilate Mesylate by Lyophilization from Tert-Butanol Dabigatran etexilate mesylate (50 mg) was dissolved in tert-butanol (t-BuOH) (5 mL) and the mixture filtered. The filtrate was frozen at −22° C. for 60 minutes, and then dried in a freeze dryer, to give amorphous dabigatran etexilate mesylate.

Example 2

Preparation of Amorphous Dabigatran Etexilate Mesylate by Lyophilization from Water Dabigatran etexilate mesylate (25 mg) was dissolved in deionized water (2 mL) and the mixture filtered. The filtrate was frozen at −22° C. for 60 minutes, and then dried a freeze dryer, to give amorphous dabigatran etexilate mesylate.

Example 3

Preparation of Amorphous Dabigatran Etexilate Mesylate by Evaporation from Methanol Dabigatran etexilate mesylate, 53 mg, was dissolved in methanol (0.25 mL) and the mixture filtered. The filtrate was evaporated using a rotary evaporator with a water bath set at 40° C., to give amorphous dabigatran etexilate mesylate.

Example 4

Preparation of Form A of Dabigatran Etexilate Mesylate by Crystallization from Ethanol Dabigatran etexilate mesylate, 30 mg, was dissolved in ethanol (EtOH) (0.15 mL) at 50° C. and the mixture filtered.

The filtrate was allowed to cool with stirring to ambient temperature, resulting in crystallisation. The solvent was evaporated under vacuum, to give dabigatran etexilate mesylate Form A.

Example 5

Preparation of Form A of Dabigatran Etexilate Mesylate by Crystallization from Ethanol with Seeding Dabigatran etexilate mesylate, 102 mg, was dissolved in ethanol (0.5 mL) at 50° C. and the mixture filtered. The filtrate was seeded with Form A of dabigatran etexilate mesylate, approx 2 mg, and allowed to cool with stirring to ambient temperature, resulting in crystallisation. The solvent was evaporated under vacuum, to give dabigatran etexilate mesylate Form A.

Example 6

Preparation of Form A of Dabigatran Etexilate Mesylate from a Mixture of Forms I and A Dabigatran etexilate mesylate, a mixture of Form I, 17 mg and Form A, 15 mg, was suspended in 2-propanol (0.6 mL) and the mixture agitated at ambient temperature using an orbital agitator for 64 hours. The mixture was filtered, dried under vacuum and analysed to be purely Form A of dabigatran etexilate mesylate as determined by powder XRD.

Example 7

Preparation of Form A of Dabigatran Etexilate Mesylate from a Mixture of Forms II and A Dabigatran etexilate mesylate, a mixture of Form II, 10 mg and Form A, 15 mg, was suspended in 2-propanol (0.6 mL) and the mixture agitated at ambient temperature using an orbital agitator for 7 days. The mixture was filtered, dried under vacuum and analysed to be purely Form A of dabigatran etexilate mesylate as determined by powder XRD.

Example 8

Preparation of Form a of Dabigatran Etexilate Mesylate from Dabigatran Etexilate Mesylate Form I Dabigatran etexilate mesylate, Form I, 50 mg, was added to acetonitrile (1 mL) with stirring, at 24° C. The product was not soluble under these conditions. The mixture was stirred for 48 hours, filtered and analysed to be Form A of dabigatran etexilate mesylate as determined by powder XRD.

Example 9

Preparation of Form A of Dabigatran Etexilate Mesylate from Amorphous Dabigatran Etexilate Mesylate Dabigatran etexilate mesylate, amorphous, 50 mg, was added to acetonitrile (1 mL) with stirring, at 24° C. with complete dissolution almost immediately. The solubility of the amorphous form is therefore >50 mg/mL. After approximately 5 minutes a solid crystallized. The mixture was stirred for 48 hours, filtered and analysed to be Form A of dabigatran etexilate mesylate as determined by powder XRD.

Example 10

Preparation of Form A of Dabigatran Etexilate Mesylate from Dabigatran Etexilate Mesylate Form I Dabigatran etexilate mesylate (106 mg, Form I) was suspended in 2-butanone (17 mL) and heated with stirring to 80° C. The mixture was seeded with dabigatran etexilate mesylate Form A (2 mg) and maintained at this temperature for a further 60 minutes. The mixture was cooled at 0.3° C./min to 25° C., maintained at this temperature for 25 minutes, filtered, washed with 2-butanone (1 mL) and dried under vacuum at ambient temperature to give dabigatran etexilate mesylate, 101 mg, as a white solid. The polymorphic form was determined by XRD to be Form A.

Example 11

Preparation of Form A of Dabigatran Etexilate Mesylate from Dabigatran Etexilate Mesylate Form I Dabigatran etexilate mesylate (148 mg, Form I) was suspended in acetone (17 mL) and heated with stirring to 56° C. The mixture was seeded with dabigatran etexilate mesylate form A (2 mg) and maintained at this temperature for a further 60 minutes. The mixture was cooled at 0.3° C./min to 25° C., maintained at this temperature for 25 minutes, filtered, washed with acetone (1 mL) and dried under vacuum at ambient temperature to give dabigatran etexilate mesylate, 129 mg, as a white solid. The polymorphic form was determined by XRD to be form A.

Example 12

Stability Assay of Dabigatran Etexilate Mesylate Form A in Acetonitrile

Dabigatran etexilate mesylate, Form A, 50 mg, was added to acetonitrile (1 mL) with stirring, at 24° C. The product was not soluble under these conditions. The mixture was stirred for 48 hours, filtered and analysed to be Form A of dabigatran etexilate mesylate as determined by powder XRD.

Example 13

Preparation of Dabigatran Etexilate Mesylate Form A from Dabigatran Etexilate Base Methanesulfonic acid (0.040 mL of a 2M solution in EtOH) was added dropwise to dabigatran etexilate base (50 mg) in EtOH (0.25 mL) at ambient temperature with stirring. The mixture was stirred for 16 hours and filtered. The solid was dried in a vacuum desiccator at ambient temperature. The product was analysed by XRD and confirmed to be Form A.

Example 14

Preparation of Dabigatran Etexilate Mesylate Form A from Dabigatran Etexilate Base Methanesulfonic acid (0.040 mL of a 2M solution in acetonitrile) was added dropwise to dabigatran etexilate base (50 mg) in acetonitrile (0.25 mL) at 50° C. with stirring. The mixture was stirred for 30 minutes and filtered. The solid was dried in a vacuum desiccator at ambient temperature. The product was analysed by XRD and confirmed to be Form A. HPLC purity: 98.3%.

Example 15

Preparation of Dabigatran Etexilate Mesylate Form A from Dabigatran Etexilate Base Methanesulfonic acid (0.040 mL of a 2M solution in n-butanol (n-BuOH)) was added dropwise to dabigatran etexilate base (50 mg) in n-BuOH (0.25 mL) at 50° C. with stirring. The mixture was stirred for 4 days and filtered. The solid was dried in a vacuum desiccator at ambient temperature. The product was analysed by XRD and confirmed to be Form A. HPLC purity: 97.8%.

Example 16

Preparation of Dabigatran Etexilate Base Form A

Dabigatran etexilate base as a 2-propanol solvate (pale yellow solid, 120 mg) was heated in methyl tert-butyl ether (MTBE) (0.7 mL) to a temperature of 60° C. The product dissolved and then after a few minutes precipitated at the same temperature. The mixture was cooled to ambient, filtered, washed with MTBE (2×1 mL+1×2 mL) to give 75 mg of a white solid. The solid was dried in a vacuum desiccator at ambient temperature. The product was analysed by XRD and confirmed to be Form A.

Example 17

Preparation of Dabigatran Etexilate Base Form A

Dabigatran etexilate base as an amorphous solid (50 mg) was heated in MTBE (0.6 mL) to a temperature of 60° C. The product dissolved and then after a few minutes precipitated at the same temperature. The mixture was cooled to ambient and filtered to give a white solid. The solid was dried in a vacuum desiccator at ambient temperature. The product was analysed by XRD and confirmed to be Form A.

REFERENCES CITED IN THE APPLICATION

WO 98/37075
WO 03/74056
WO 2005/028468
WO 2011/110876
WO 2011/110478

Assessment Report for Pradaxa of the Committee for Human Medicinal Products (CHMP) of the European Medicines Agency (EMEA/174363/2008)

The invention claimed is:

1. A crystalline Form A of dabigatran etexilate mesylate characterized by having an X-ray diffractogram that comprises characteristic peaks at 4.4, 8.9, 9.8, 12.3, 17.8, 18.4, 19.2, 19.7, 21.4, 23.4, 27.3, 28.2±0.1 degrees 2 theta measured in an X-ray diffractometer with Cu Kα radiation (1.5418 Å).

2. A pharmaceutical composition comprising an effective amount of the crystalline Form A of dabigatran etexilate mesylate as defined in claim 1, together with one or more pharmaceutically acceptable excipients or carriers.

3. A process for the preparation of the crystalline Form A of dabigatran etexilate mesylate as defined in claim 1, comprising:
   a) providing a solution of dabigatran etexilate mesylate in an organic solvent;
   b) optionally seeding with dabigatran etexilate mesylate, Form A; and
   c) isolating the crystalline Form A of dabigatran etexilate mesylate from the reaction medium.

4. The process according to claim 3, wherein step a) is performed in an organic solvent selected from the group consisting of ethanol, n-butanol and acetonitrile at a temperature comprised between 0° C. and the reflux temperature of the solvent.

5. A process for the preparation of the crystalline Form A of dabigatran etexilate mesylate as defined in claim 1, comprising:
   a) providing a suspension of dabigatran etexilate mesylate, which is a pure solid form or a mixture of solid forms, in an organic solvent;
   b) optionally seeding with dabigatran etexilate mesylate, Form A; and
   c) isolating the crystalline Form A of dabigatran etexilate mesylate from the reaction medium.

6. The process according to claim 5, wherein step a) is performed in an organic solvent selected from isopropyl alcohol, acetonitrile, acetone and 2-butanone at a temperature comprised between 0° C. and the reflux temperature of the solvent.

* * * * *